Figure 1:
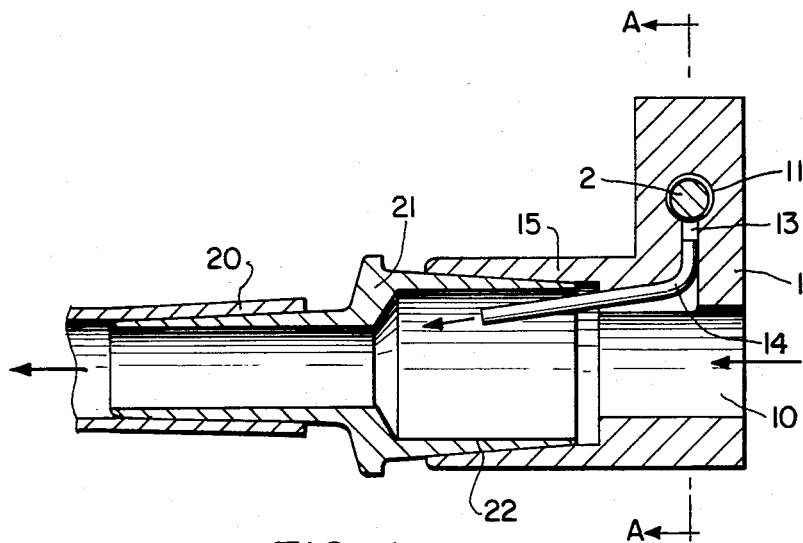

United States Patent [19]

Lemer

[11] Patent Number: 4,495,946
[45] Date of Patent: Jan. 29, 1985

[54] ARTIFICIAL BREATHING DEVICE

[76] Inventor: Joseph Lemer, 15 Bracha-Habas St., Haifa, Israel, 33393

[21] Appl. No.: 244,751

[22] Filed: Mar. 17, 1981

[51] Int. Cl.³ .............................................. A61M 16/00
[52] U.S. Cl. .......................... 128/204.25; 128/205.11; 128/205.24; 128/204.21
[58] Field of Search ...................... 128/207.14, 207.15, 128/204.25, 203.11, 205.24, 203.12, 203.25, 204.21, 205.11, 6, 11, 200.21

[56] References Cited

U.S. PATENT DOCUMENTS

| 2,280,050 | 4/1942 | Alexander et al. | 128/203.11 |
| 3,319,627 | 5/1967 | Windsor | 128/204.25 |
| 3,628,532 | 12/1971 | Magrath | 128/204.25 |
| 3,881,479 | 5/1975 | Carden | 128/207.15 |
| 3,964,488 | 6/1976 | Ring et al. | 128/207.14 |
| 4,030,492 | 6/1977 | Simbruner | 128/200.21 |
| 4,224,940 | 9/1980 | Monnier | 128/204.25 |
| 4,265,237 | 5/1981 | Schwanbom et al. | 128/204.25 |
| 4,270,778 | 6/1981 | Brownell | 128/207.14 |

FOREIGN PATENT DOCUMENTS

| 808824 | 10/1961 | United Kingdom . |
| 951724 | 3/1964 | United Kingdom . |
| 1076767 | 7/1967 | United Kingdom . |
| 1218137 | 1/1971 | United Kingdom . |
| 1425039 | 2/1976 | United Kingdom | 128/204.25 |
| 2025239 | 1/1980 | United Kingdom . |

Primary Examiner—Henry J. Recla
Attorney, Agent, or Firm—Schwartz, Jeffery, Schwaab, Mack, Blumenthal & Koch

[57] ABSTRACT

A device for artificial respiration is attached by an unobstructed air duct to the outer end of a flexible endotracheal tube or to a breathing mask. It is provided with a regulating valve which has its inlet side connected to an oxygen supply via an "on-off" time-cycling apparatus of known design, while its outlet side is connected to the air duct through a small-bore tube which extends close and parallel to the air duct wall in the direction towards the mask or the endotracheal tube. Oxygen passing through the small-bore tube into the air duct at great velocity draws air from the outside by injector action and presses it into the lungs of a patient. Upon the end of the "on"-cycle the air is expelled by the elasticity of the lungs and of the chest cavity and can freely escape through the unobstructed air duct, which likewise permits the ejection of mucus, blood and other excretions.

7 Claims, 4 Drawing Figures

ARTIFICIAL BREATHING DEVICE

The invention relates to a device for causing artificial respiration through an endotracheal tube or through a breathing mask.

With certain diseases and during specific operations it becomes necessary to perform direct artificial respiration by pumping air or oxygen into the patient's lungs, which then is exhaled by the natural elastic recoil of the walls of the chest cavity and the lungs. The method used at present consists in introducing a flexible tube into the trachea or the windpipe and to supply air or oxygen at predetermined intervals and to interrupt the pressure for the exhalation period. Air or oxygen is introduced into the lungs by means of an air pump or bellows, either mechanically or manually operated at a suitable rhythm, while the exhaled air escapes through a separate exhaust valve which opens during the return stroke of the pump or bellows. This is important in order to prevent mixing of the contaminated, exhaled air with the fresh air or oxygen to be pressed into the lungs.

The drawback of this method and apparatus is its clumsiness and the difficulty in adjusting the air pressure and quantity to the patient's age and condition. Another drawback is that the flexible tube is substantially closed, except for the exhaust valve which, in general, does not permit the removal of mucus and other excretions.

A medical instrument which is provided with an auxiliary breathing device, is the bronchoscope consisting of a rigid tube with a small bulb at its end, through which the bronchi or the windpipe can be examined and foreign bodies can be removed. In order to promote breathing, a capillary tube is inserted into the rigid tube adjacent its wall, with its open and directed towards the portion inserted into the traches, through which oxygen is blown at high velocity at intervals corresponding to the breathing rhythm. This jet of oxygen acts as an injector and drives air into the lungs through the rigid tube, otherwise leaving the passage free for inspection and manipulation of instruments. For patients of different age and condition different sizes of capillary tubes are inserted with a view to obtaining the necessary air velocity and quantity.

The rigid tube permits the retaining of the instrument in the trachea for a relatively short time only; its other drawback is the necessity of having to chose and interchange different sizes of capillary tubes for each patient.

Similar conditions prevail in the use of breathing masks which may be required to provide artificial respiration to patients for several hours. In case of gas poisoning it will be frequently necessary to provide artificial respiration to a large group of people simultaneously who were affected, especially in war or as a result of a catastrophe; in these cases each mask has to be provisioned with the correct quantity of oxygen and air, dependent on the age and condition of each person. At present this is obtained by installing a pressure reduction valve and a manually or electronically monitored cycling device in the line from an oxygen cylinder to the mask, which not only represents a costly investment, but requires constant supervision.

It is, therefore, an object of the present respiration device to provide individual adjustment of the oxygen-air quantity to be administered to each patient, but to utilize a common supply of compressed oxygen and a common cycling apparatus for a whole group of patients, with the aim to simplify and to reduce the cost of the necessary equipment.

In addition, with a view to overcome drawbacks of the existing apparatus, the breathing device according to the present invention has been developed by utilizing part of the previous concepts, but in a combination that is completely novel and gives satisfactory and surprising results.

The respiration device, according to the present invention, comprises: a valve housing containing an inlet opening provided with means for connecting it to a time-cycled source of compressed air or oxygen; a regulating valve consisting of a valve stem, preferably a needle valve stem, adapted to be manually adjusted in such a manner as to permit a predetermined quantity of air or oxygen to pass through said valve housing to an outlet opening, the latter being connected to a rigid tube of small diameter.

The valve housing further contains an air duct of a diameter large in comparison with said rigid tube, one end of which is open to the atmosphere, while its other end is provided with means for connecting it to a breathing mask or to a flexible tube of a kind suitable for insertion into the trachea. The rigid tube extends from the valve outlet into the air duct substantially coaxial with the duct axis, close to the duct wall and with its open outlet end directed towards its connection with the flexible tube or the breathing mask. Air or oxygen passing from the supply through the valve and the rigid tube at great velocity, draws air from the outside through the flexible tube into the lungs by injector action as known to the art. The air or oxygen is cycled, manually or by means of an electronic circuit, which can be adjusted in accordance with the desired breathing rhythm and frequency. As soon as the compressed air supply stops at the end of each cycle, the elasticity of the lungs and the chest cavity drive the spent air into the open, as in the case of a breathing mask. When the apparatus is attached to an endotracheal tube the air is expelled through this tube together with mucus, blood or other discharges which can pass or can be aspirated into the open without any obstruction in their path.

In one of the embodiments of the respiration device, the regulating valve is in the shape of a needle valve which permits very accurate dosing, but does not lend itself to visual perception of the position of the valve stem in relation to the valve seat, i.e. the magnitude of the valve opening.

In another embodiment the regulating valve is in the shape of a gauge cock, which gives somewhat less accurate results than a needle valve, but permits the indication of its relative opening on an outside disc serving to turn the cylindrical perforated cock into the angular position corresponding to the required gas quantity.

To prevent contamination it is often necessary to provide separate ducts for the inhaled and exhaled air, and the present respiration device may - for this purpose - be fitted with one of the known kinds of one-way inhaling-exhaling valves (Ruben valve).

For certain kinds of diseases it is also necessary to have the air expelled out of the lungs against a predetermined counter-pressure; the present device permits the installation in the exhalation port of the three-way valve of such counterpressure device, which is known as PEEP (positive end expiratory pressure).

In addition, the outside air may be let into the apparatus, and from there into the lungs, through an air filter which can be readily fitted to the inlet side of the air duct.

Figure 2:
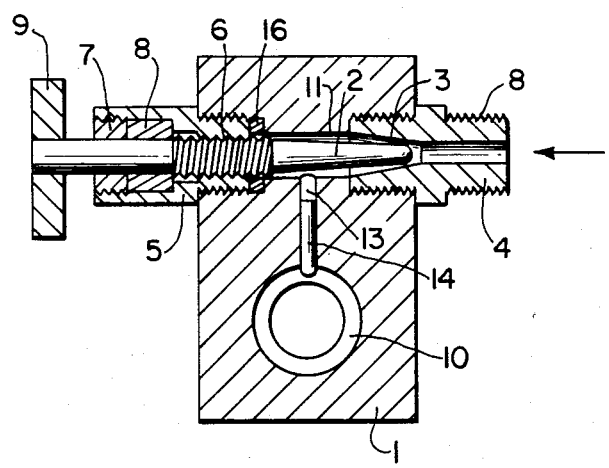
Figure 3:
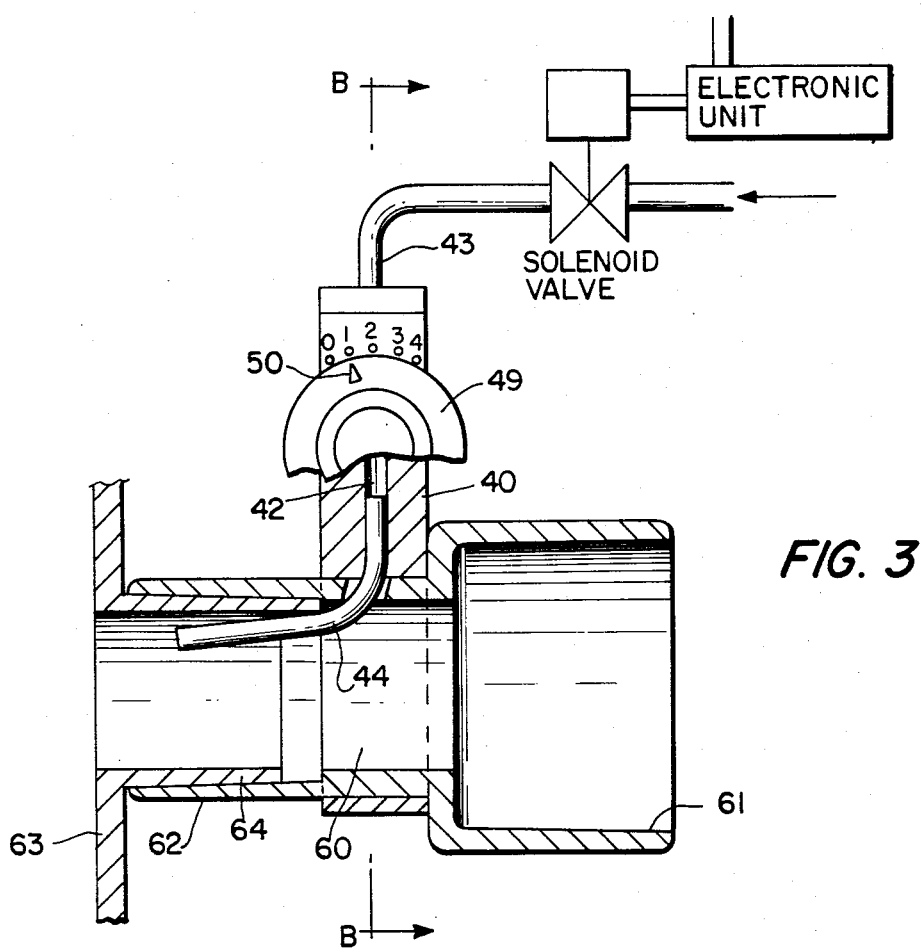
Figure 4:
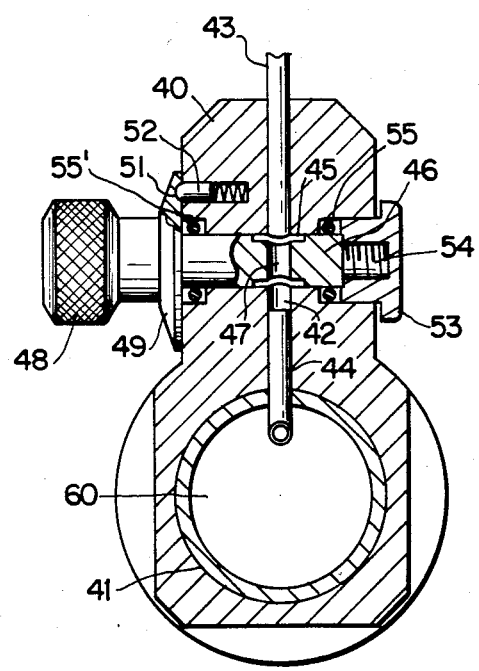

In the accompanying drawings which illustrate, by way of example, two embodiments of the invention, FIG. 1 is a longitudinal section through the artificial respiration device and through an attached flexible tube, FIG. 2 is a section along A—A of FIG. 1, FIG. 3 is part elevation and part section through a second embodiment of the respiration device, which is attachable to a breathing mask, and FIG. 4 is a section along B—B of FIG. 3.

Referring to FIGS. 1 and 2 of the drawing, a valve housing is perforated in its upper part by a valve bore 11 and in its lower part by an air duct 10 distanced therefrom, the two bores lying in two parallel planes with their axes crossing at a right angle. The two bores communicate by means of a connecting bore 13 centrally positioned in the valve housing. The valve bore is provided at its both ends, adjoining the housing sides, with screw thread which holds at one end a double nipple 4, and at its other end a valve guide 5 and a gasket 16. The double nipple is centrally perforated and is shaped to form a valve seat 3 in the shape of a hollow cone frustum positioned inside the housing, while its outside is screw-threaded for the connection to a high-pressure air or oxygen supply. The valve guide is provided with fine inner thread 6 and with a gland 7 serving to compact a gasket packing 8. A valve stem 2 is inserted in the bore 11 and guided in the valve guide 5, being provided with a conical end corresponding to the valve seat 3. The centre portion of the stem is provided with fine thread corresponding to the thread 6 in the valve guide which permits the moving of the valve stem in relation to the stationary valve seat, by rotating it with the aid of a knob 9 fastened to the outer end of the stem.

The air duct is continued beyond the valve housing proper to form a sleeve 15 having a conical inner surface. A flexible tube 20 mounted on a tubular coupler 21 is firmly attached to the sleeve 15 by means of a frustoconical section 22 inserted into the sleeve. A rigid tube 14 of a small inner bore is inserted with its one open end into the connecting bore 13 and is bent to an angle of about 100°, whereby the other open end projects into the section 22 of the tubular coupler 21, close to its inner wall.

Since flexible tubes of different diameter are required for different patients, it will be understood that each flexible tube comes supplied with its appropriate coupler, all couplers being provided with the same size cone so as to enable their connection to the valve housing by means of the sleeve 15. In accordance with the valve opening a predetermined quantity of oxygen or air will flow through the tube 14 into the coupler space, drawing atmospheric air through the air duct into the flexible tube and into the lungs, by injector action in a known manner.

The breathing device of FIGS. 3 and 4 is in most aspects identical with that of FIGS. 1 and 2, except for a different type of valve incorporated therein and for a socket serving for the attachment of a one-way inhaling-exhaling valve or a filter. The device consists of two separate, tightly connected parts, a valve housing 40 and an air duct 60, the latter being fitted into a circular bore 41 in the valve housing. The valve housing is centrally perforated by a bore 42 which contains an oxygen connecting pipe at its outer end and a small-bore, angularly bent tube 44 at its inner end, which tube extends into the air duct 60 through a suitable perforation and runs substantially parallel to the duct wall. The valve housing comprises a valve seat in the shape of a bore 45, crossing the central bore 42 at a right angle and containing the cylindrical stem 46 of a gauge cock. The stem is transversely perforated by a bore 47 in a position corresponding to the central bore 42 whereby the oxygen passage through the valve can be regulated in accordance with its angular position relative to the bore 42. The gauge cock is turnable by means of a knob 48 at its outer end, into one of five positions 0,1,2,3,4, defining a gradually diminishing gas passage, down from a maximum when the axes of the bores 42 and 47 coincide. The knob is continued and enlarged into a flat disc 49 adjacent the valve housing exterior and is provided with a mark which points to the respective figure 0 to 4 in accordance with its angular position. The disc is provided on the side adjacent the valve housing with indentations 51 which are adapted to engage with a spring catch 52 set in a bore in the valve housing and destined to hold the gauge cock in its required angular position.

The valve stem is held in axial position by a cap 53 which engages with the end of the stem by means of screw thread 54. Two O-ring seals 55 and 55' prevent gas from escaping to the outside.

The air duct 60 is provided with an outer tapered socket 61 which serves to connect to the device a three-way inhaling-exhaling valve, or a filter. The other end of the air duct forms an inner tapered socket 62 which serves to connect to it a flexible tube of the kind described with reference to FIG. 1 or a breathing mask 63 which - for this purpose - is provided with a nipple 64, correspondingly tapered.

The air or oxygen is supplied from a high-pressure source, preferably a gas cylinder, via a solenoid valve or a similar valve monitored by an electronic circuit. This circuit is programmed regarding the frequency and duration of each breathing cycle permitting a very accurate and unchanging artificial respiration of the patient. It will be understood that, as an alternative, the operation of the oxygen valve can be carried out manually by a skilled nurse, in case of a breakdown, or should irregular breathing become necessary.

The main advantage of the artificial breathing device is its completely open passage which permits blood, mucus or other excretions to be freely discharged into the open. Another, very important aspect of the invention is the possibility to provide artificial respiration to several patients simultaneously from one common oxygen source, through one single solenoid valve monitored by an electronic circuit; hereby the breathing rhythm remains identical for all patients, the air quantity, however, can be individually adjusted for each patient by means of the regulating valve provided in the device.

This feature applies both to an endotracheal tube as to breathing masks, an important feature in war time or in other emergencies.

I claim:

1. A device for artificial respiration adapted to introduce predetermined quantities of air or oxygen into the lungs at predetermined intervals, comprising: an automatic time-cycled source of air or oxygen; a valve housing containing an inlet passage connected to said time-cycled source of compressed air or oxygen; a manually adjustable regulating valve mounted within said inlet passage to throttle said inlet opening and to be manually adjusted to the required air or oxygen quantity; and an air duct perforating said valve housing distanced from said regulating valve and having its one end open to the atmosphere during the introduction of said respirating gas into said lungs, while its other end is provided with means for attaching to it a patient; a rigid, small bore tube having one end connected to said air duct and an opposite end connected to said passage downstream said regulating valve, said tube entering said air duct downstream of said regulating valve and extending close to the wall of said air duct with its open end directed in the direction of said attaching means, said small bore tube being dimensioned such that a venturi effect is created when said compressed air or oxygen passes through said small bore tube, whereby said timed-cycled source forces air or oxygen through said small bore tube creating a venturi effect drawing atmospheric air into said duct through said open end and forcing a mixture of said atmospheric air and said air or oxygen from said source into the lungs of said patient.

2. The device for artificial respiration of claim 1, wherein said patient attaching means comprises a flexible endotracheal tube and a coupler connected at the end of said flexible endotracheal tube, said coupler comprising a first frusto-conical portion, said housing having a second frusto-conical portion frictionally engaging with said first frusto-conical portion, one of said first and second frusto-conical portions being a male portion and the other of said frusto-conical portions being a female portion.

3. The device for artificial respiration of claim 2, wherein said coupler frusto-conical portion is formed on one end of said coupler and said coupler has a frusto-conical end with means for connection to said endotracheal tube.

4. The device for artificial respiration of claim 1, wherein said regulating valve comprises a needle valve.

5. The device for artificial respiration of claim 1, wherein said regulating valve comprises a gauge cock.

6. The device for artificial respiration of claim 1, wherein the inlet passage is connected to a solenoid valve positioned in the line from said source of compressed air or oxygen and monitored by an electronic unit.

7. The device for artificial respiration of claim 1, wherin said one end and said other end of said air duct are aligned with each other.

* * * * *